United States Patent [19]

Pilloff

[11] 3,995,957
[45] Dec. 7, 1976

[54] INTERNALLY REFERENCED, LASER INTRACAVITY TECHNIQUE FOR MEASURING SMALL GAINS OR LOSSES

[75] Inventor: Herschel S. Pilloff, Oxon Hill, Md.

[73] Assignee: The United States of America as represented by the Secretary of the Navy, Washington, D.C.

[22] Filed: Oct. 16, 1975

[21] Appl. No.: 623,143

[52] U.S. Cl. .......................... 356/114; 331/94.5 R
[51] Int. Cl.² ..................... G01N 21/40; H01S 3/00
[58] Field of Search ........................ 356/114–115, 356/116–119, 206; 331/94.5 R, 94.5 C, 94.5 G

[56] References Cited
UNITED STATES PATENTS

| | | | |
|---|---|---|---|
| 3,653,767 | 4/1972 | Liskowitz | 356/114 |
| 3,926,524 | 12/1975 | Margulies et al. | 356/114 |

OTHER PUBLICATIONS

Tsuda, M. "Apparatus for Rapid Measurement of Optical Rotation Changes," Rev. of Scientific Instruments vol. 46, 10–1975, pp. 1419–1420.

Rowell et al. "Depolarization of Light Scattered by Gases from Rotating Analyzer Measurements & A Ratio Method of Analysis" Jr. of Colloid & Interface Science vol. 39, 6–1972, pp. 472–478.

Primary Examiner—Edward S. Bauer
Assistant Examiner—Wm. H. Punter
Attorney, Agent, or Firm—R. S. Sciascia; Philip Schneider; Melvin L. Crane

[57] ABSTRACT

A method and system for measuring small gain or losses in a laser cavity. The method includes placing a sample in a cell in a two beam system in which one beam polarized in one direction passes through the cell while the other beam of different polarization does not pass through the cell. The ratio of the two polarizations with the sample in and out of the cell in the system determines a measure of the effect of the sample on the system. The ratios are measured with the sample cell empty and then with the sample in the cell.

3 Claims, 1 Drawing Figure

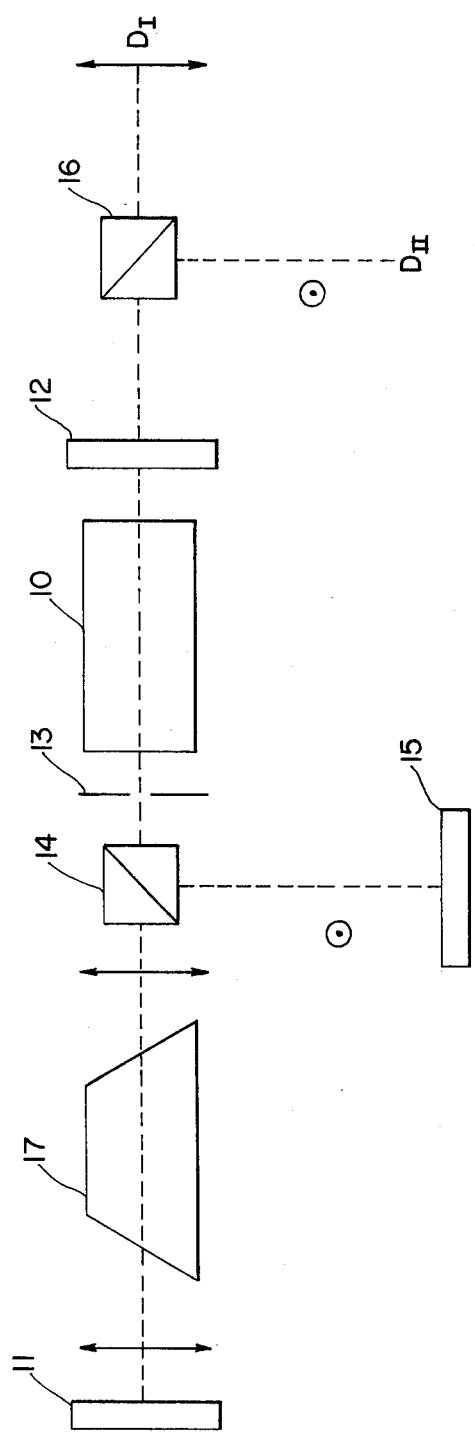

INTERNALLY REFERENCED, LASER INTRACAVITY TECHNIQUE FOR MEASURING SMALL GAINS OR LOSSES

BACKGROUND OF THE INVENTION

This invention relates to laser systems and more particularly to a method and means for measuring small gains or losses within the optical cavity of a laser.

Heretofore intracavity techniques for measuring small gain or losses in a laser cavity have involved inserting an optical sample within the laser resonator and observing any changes (increases or decreases) in the laser output. By this system, the sensitivity is approximately determined by the random gain fluctuations of the laser. This presents a limitation on the laser operation particularly in the case of some pulse lasers.

SUMMARY OF THE INVENTION

A solid state, gas or dye laser is operated normally in a laser cavity which includes a polarizer on opposite sides of the laser element for simultaneous two wave operation at one wavelength but with mutually perpendicular polarizations. The polarizer on the output side of the laser element directs each polarization to different appropriate detectors. The ratios of the intensities at the detectors $I_1/I_2$ are determined without and then with a sample material in a cell in the cavity. The intracavity polarizer on the full reflective side of the laser element diverts the perpendicularily polarized beam away from the sample cell to a fully reflecting mirror. Therefore only the horizontally polarized beam passes through the sample cell. If the ratio of the signal at the detectors increases when the sample is added, then the sample is contributing a net gain, conversely a decreased ratio indicates absorption or a loss.

BRIEF DESCRIPTION OF THE DRAWING

The DRAWING is a block diagram of the system including a sample cell in the system.

DETAILED DESCRIPTION

Now referring to the drawings, there is illustrated by block diagram a laser system illustrating this invention. As shown, the system includes a solid state, gaseous or dye laser medium 10 in a cavity with a fully reflective mirror 11 and an output coupling partially reflective mirror 12. An aperture 13 for $TEM_{oo}$ operation is placed adjacent to the end of the laser medium on the side with the fully reflective mirror. An intracavity polarizer such as a Glan prism 14 is placed between the aperture and the fully reflective mirror 11 which operates to pass horizontally polarized radiation, noted by the , to the fully reflective mirror 11 while reflecting the perpendicularly polarized beam, noted by 0, 90° onto a fully reflective mirror 15. A polarizer such as a Glan prism 16 is placed in the output beam to direct the horizontally polarized beam onto a detector $D_1$ on the optical axis while directing the perpendicularly polarized beam 90° onto a detector $D_2$. A sample cell 17 is included in the cavity between the Glan prism 14 and the fully reflective mirror 11. The ends of the sample cell are at Brewster's angle as well known in the art. When the sample is a gas, the system is operated with the sample cell empty and ratio of the detectors are taken, then the gas sample is placed in the sample cell and the ratio of the detectors are taken. The difference in the ratios will determine whether there is a gain or a loss. If the sample is other than gas it will be necessary to use some sort of blank material in the sample cell for measuring the first ratio. The reason for this is that the reflection losses for the sample cell will change dramatically when it is empty or evacuated as compared to the time when it contains a sample other than gas for example a liquid. In both instances, the losses at the glass windows will be the same, however, the losses at the surfaces of the material within the sample cell depend on the differences in the indices of refraction between the glass windows and the sample. If the cell is empty or evacuated the index of refraction is substantially unity. If it has a low pressure gas, the index is substantially unity. However, liquids and solids are different. If a liquid sample cell may first be checked with a "blank" solution of pure water so as to allow the reflection losses within the cell to be nulled when the blank solution is removed and replaced with the sample of interest. The system is operated without any material in the cell or a blank in the cell and then with an appropriate test material in the cell depending upon the test material. An appropriate material is a material of which one wants to determine whether the material will produce a gain or a loss in the laser system.

With the above described system the laser operates with two beams simultaneously at one wavelength but with mutually perpendicular polarizations. The ratios of the radiation intensities for each polarization at the detectors is $I_1/I_2$.

In order to determine whether a sample of a desired medium will increase or decrease the output, a detector ratio, $I_1/I_2$, is first obtained with a sample cell 17 in the cavity without the medium therein, with the cavity placed in the horizontally polarized beam between the fully reflective mirror 11 and the Glan prism 14. Then the sample is placed into the sample cell and a ratio is obtained with the sample in the cell.

An increase in the ratio denotes a net gain and a decrease in the ratio indicates absorption or a loss. The sample cell is shown with the end windows at Brewster's angle for minimizing reflection of in plane polarization from outside surfaces of the cell windows and also for inside surfaces when used with gases. By placing the sample cell in only the path of the horizontally polarized beam, the system provides its own internal reference; that is, the intensity of the perpendicularly polarized beam component which does not pass through the sample cell.

In this system, the effect of the gain fluctuations is compensated by ratioing. For ratios close to unity, the two intensities change proportionately, but the ratios remain constant resulting in an improved sensitivity.

It is further believed that polarization competition effects occur in the simultaneous two-polarization laser system. The consequence of polarization competition is that when the component passing through the sample cell is increased or decreased as a result of the material in the cell the other component that does not pass through the sample cell will undergo an opposite change (increase or decrease). The result is that any change due to the sample will further drive the ratio from unity. Thus, the sensitivity of the method will be enhanced by polarization competition effects. The above described system is believed to provide a new combination of simultaneous operation of the laser with well defined mutually perpendicular polarizations with spatial separation of the polarization within the laser cavity. Further, one polarization is utilized to provide an internally produced reference wherein the other polarization is utilized for determining gain or loss in the sample and the utilization of polarization competition effects to enhance any loss or gain introduced by the sample.

The system has been shown with fully reflective mirrors 17 and 15. It is to be noted that any suitable frequency selective elements may be used as required so long as the elements are tuned to the transition of interest.

Obviously many modifications and variations of the present invention are possible in light of the above teachings. It is therefore to be understood that within the scope of the appended claims the invention may be practiced otherwise than as specifically described.

What is claimed and desired to be secured by Letters Patent of the United States is:

1. A method for measuring small gain or losses in a laser cavity; which comprises:
    operating the laser simultaneously at one wavelength but with a perpendicular polarized and a horizontally polarized radiation beams;
    directing each polarization to separate detectors;
    determining the ratio of the radiation intensities detected at each detector with a sample cell in the horizontal polarized beam;
    placing a desired material within said sample cell, and determining the ratio of the radiation intensities with the material in the cell to determine any increase or decrease in the ratio;
    wherein an increase in the ratio indicates a gain and a decrease indicates a loss.

2. A method as claimed in claim 1, wherein the material placed in said cell is a gaseous medium whose optical properties are of interest.

3. A system for measuring small gain or losses in a laser cavity, which comprises:
    a laser medium having first and second ends;
    a first fully reflective mirror opposite said first end of said laser medium;
    a partially reflective mirror opposite said second end of said laser medium;
    a mode selector aperture adjacent said first end of said laser medium;
    whereby a comparison of the ratios of the measured intensities in the output beam of the horizontally polarized radiation to the measured intensities of the perpendicularly polarized radiation with a sample in said sample cell to that of the ratio without a sample in the cell determines gain or loss in the system due to the sample.
    an intracavity polarizer between said aperture and said fully reflective mirror for passing horizontally polarized radiation to said first totally reflective mirror and reflecting perpendicularly polarized radiation at an angle thereto;
    a sample cell between said intracavity polarizer and said fully reflective mirror;
    a second fully reflective mirror for receiving and reflecting said perpendicularly polarized radiation from said intracavity polarizer;
    a second polarizer in the output of said laser medium opposite said partially reflective mirror for passing horizontally polarized radiation and for reflecting perpendicularly polarizes radiation at an angle thereto;
    a detector opposite said second polarizer for measuring the intensity of said horizontally polarized radiation, and
    a detector for measuring said perpendicularly polarized radiation reflected from said second polarizer.

* * * * *